(12) United States Patent
Hornegger et al.

(10) Patent No.: US 7,536,040 B2
(45) Date of Patent: May 19, 2009

(54) METHOD FOR GENERATING A 3D IMAGE DATASET

(75) Inventors: Joachim Hornegger, Baiersdorf (DE); Joachim Reiss, Baiersdorf (DE)

(73) Assignee: Siemens Aktiengesellschaft, Munich (DE)

( * ) Notice: Subject to any disclaimer, the term of this patent is extended or adjusted under 35 U.S.C. 154(b) by 901 days.

(21) Appl. No.: 10/465,104

(22) Filed: Jun. 19, 2003

(65) Prior Publication Data

US 2004/0041807 A1 Mar. 4, 2004

(30) Foreign Application Priority Data

Jun. 19, 2002 (DE) ................ 102 27 307

(51) Int. Cl.
*G06K 9/00* (2006.01)

(52) U.S. Cl. ............... 382/128; 378/2; 378/4; 378/21; 378/28

(58) Field of Classification Search ......... 382/128–132, 382/154, 285; 378/1–28
See application file for complete search history.

(56) References Cited

U.S. PATENT DOCUMENTS

| | | | | |
|---|---|---|---|---|
| 4,744,029 A | * | 5/1988 | Raviv et al. ............... 600/544 |
| 5,482,043 A | * | 1/1996 | Zulauf ...................... 600/437 |
| 5,550,376 A | * | 8/1996 | Gupta et al. ............ 250/360.1 |
| 5,558,638 A | * | 9/1996 | Evers et al. .................. 604/66 |
| 5,603,323 A | * | 2/1997 | Pflugrath et al. .......... 600/437 |
| 5,655,084 A | * | 8/1997 | Pinsky et al. ................ 705/3 |
| 5,715,823 A | * | 2/1998 | Wood et al. ............... 600/437 |
| 5,807,256 A | * | 9/1998 | Taguchi et al. ............ 600/425 |
| 5,851,186 A | * | 12/1998 | Wood et al. ............... 600/437 |
| 5,949,491 A | * | 9/1999 | Callahan et al. ........... 348/442 |
| 5,963,613 A | * | 10/1999 | Navab ......................... 378/4 |
| 5,976,088 A | * | 11/1999 | Urbano et al. ............. 600/443 |
| 5,987,519 A | * | 11/1999 | Peifer et al. ............... 709/230 |
| 6,050,940 A | * | 4/2000 | Braun et al. ............... 600/300 |
| 6,055,487 A | * | 4/2000 | Margery et al. ............. 702/84 |
| 6,081,577 A | * | 6/2000 | Webber ..................... 378/23 |
| 6,101,407 A | * | 8/2000 | Groezinger ................ 600/407 |
| 6,118,845 A | * | 9/2000 | Simon et al. ............... 378/62 |
| 6,157,853 A | * | 12/2000 | Blume et al. .............. 600/426 |
| 6,259,943 B1 | * | 7/2001 | Cosman et al. ............ 600/429 |
| 6,307,914 B1 | * | 10/2001 | Kunieda et al. ............. 378/65 |
| 6,683,933 B2 | * | 1/2004 | Saito et al. ................... 378/4 |
| 6,721,590 B2 | * | 4/2004 | Ohishi et al. .............. 600/431 |
| 2002/0085668 A1 | * | 7/2002 | Blumhofer et al. .......... 378/68 |
| 2002/0122536 A1 | * | 9/2002 | Kerrien et al. ............ 378/205 |
| 2002/0151781 A1 | * | 10/2002 | Ohishi et al. .............. 600/407 |
| 2003/0156745 A1 | * | 8/2003 | Saito et al. ................ 382/128 |
| 2004/0030585 A1 | * | 2/2004 | Sariel .......................... 705/3 |

OTHER PUBLICATIONS

"Three-Dimensional medical Visualisation Bound to Break The Limits Of Diagnostics and Treatment," Versweyveld, Virtual Medical World Monthly, May 2001.
"Bildgebende Systeme für die Medizinische Diagnostik," Morneburg, 1985, pp. 684-696.
"The Application Service Providers in Healthcare," Emig et al, electromedica 69 (2001), vol. 1, pp. 2-4.

* cited by examiner

*Primary Examiner*—Matthew C Bella
*Assistant Examiner*—Manav Seth
(74) *Attorney, Agent, or Firm*—Schiff Hardin LLP

(57) ABSTRACT

In a method for the generation of a 3D dataset from 2D x-ray datasets, the 2D data are forwarded from a customer to a 3D reconstruction center in which a calibration of the projection geometry ensues by means of a software package and/or a specialist. As a result a 3D volume dataset is calculates and made available to the customer.

12 Claims, No Drawings

METHOD FOR GENERATING A 3D IMAGE DATASET

BACKGROUND OF THE INVENTION

1. Field of the Invention

The invention concerns a method for generating a 3D dataset from 2D x-ray recordings that require elaborate calibrations of a C-arm system used to generate the 20 datasets. It is desirable for a reconstruction of this type to ensue on a standard computer that is networked with the x-ray installation, however, the 3D option is not available on many installations and an offline reconstruction cannot be done because no calibration data are available.

2. Description of the Prior Art

Although methods exist to calculate the projection parameters from datasets obtained without calibration samples, they are not 100% dependable or may not be numerically possible under the circumstances, since the projections are recorded nonlinearly.

A Picture Archiving and Communication System (PACS) for the treatment of acquired image data and the visualization of volume date is described in the article "Three-Dimensional Medical Visualization Bound To Break The Limits Of Diagnostics And Treatment", by Leslie Versweyveld, Virtual Medical World Monthly, May 2001. Visualization refers to a class of algorithms that allow image data to be visualized on a monitor. For example, a volume renderer forms a 3D volume that can then be presented on a 2D monitor from a 2D image.

SUMMARY OF THE INVENTION

An object of the invention is to provide a method for the reconstruction of a 3D dataset for users of simple C-arm systems that are not equipped to derive such a 3D volume dataset as needed from 2D x-ray recordings. As used herein, a U.S.P.Q.2d x-ray recording means the x-ray image itself or a dataset representing the image.

This object is achieved in accordance with the invention in a method wherein the 2D recordings from a customer are forwarded to a 3D reconstruction center, in which a calibration of the projection geometry ensues by means of a software package and/or by a specialist, and as a result a 3D volume dataset is calculated and made available to the customer.

By the inventive relocation of the generation of a 3D dataset to a suitably equipped reconstruction center, every user of a C-arm system can have such a 3D dataset prepared as needed without the expensive and elaborate installation for the generation of a 3D dataset, by the customer sending the 2D x-ray recordings to the reconstruction central in various manners. In addition to the possibility to burn the data on a CD and to forward this and, if necessary, the 2D x-ray recording itself, through the mail to the reconstruction central, it is especially practical for the customer to be connected to the reconstruction central via the Internet, so that the customer can electronically transmit 2D datasets and download the desired results via the Internet.

As used herein, reconstruction means a class of algorithms that calculate the original data (i.e. before the projection) from the projection data recorded from various directions. For example, the result of the 3D reconstruction from 2D projections is a volume dataset.

In addition to the possibility of the creation of a 3D volume (for example, in DICOM), the reconstruction center can create a video of the rendered dataset, or make specially rendered individual exposures of the 3D dataset available.

A software package and/or a specialist using this data effects a calibration of the project geometry in the reconstruction center, which can ensue in various manners:

DESCRIPTION OF THE PREFERRED EMBODIMENTS

Many physicians have, in their office or clinic, access to an x-ray imaging system which is capable of generating two-dimensional (2D) x-ray images or x-ray image datasets. For many everyday applications, such two dimensional x-ray images are sufficient for the physician's needs, however, occasionally the physician may have a need for making a diagnosis based on a three-dimensional image. Since a software package to produce such a three-dimensional image from multiple 2D projections is relatively expensive, it is not cost-justified for the physician to purchase such a package only for such occasional uses. In accordance with the invention, when the physician has a need for making a diagnosis based on a three dimensional image, the physician communicates multiple sets of 2D projection data, or possibly the x-ray images themselves, to a reconstruction center, which is remote from the location of the physician. The reconstruction center has the computational capability of generating a three-dimensional image from multiple 2D projection datasets. After the reconstruction center generates the three-dimensional image, the data representing this three-dimensional image are communicated back to the physician.

For generating the three-dimensional image, it is necessary to reference the respective 2D projections relative to each other, in terms of their spatial relationship (calibration). There are several techniques available for undertaking this step.

An autocalibration can ensue at the reconstruction center in such a manner that natural landmarks are automatically detected and point correspondences calculated with image processing methods (segmentation). The 3D coordinates of the points as well as the projection parameters (extrinsic and intrinsic camera parameters) are subsequently assessed.

In a further autocalibration, natural landmarks are manually detected and the point correspondences calculated with image processing methods (segmentation) at the reconstruction center. The 3D coordinates of the points as well as the projection parameters are again subsequently assessed.

In a third embodiment of an autocalibration, markers are applied to the patient when the 2D projections are obtained and these markers are automatically detected and the point correspondences calculated with image processing methods (segmentation) at the reconstruction center. The 3D coordinates of the points as well as the projection parameters (extrinsic and intrinsic camera parameters) are again subsequently assessed.

Calibration with a reference sample can also ensue, by a calibration sample with known 3D geometry being located together with the patient data in the exposure. The point features are automatically detected and the point correspondences are calculated. Again, the assessment of the project parameters ensues with known 3D geometry.

An advantage of the inventive method is that the customer is given the possibility to have a 3D volume dataset generated via the Internet, even without a 3D package. This is important for the presentation of interesting, scientific, and new medical applications. The inventive method, however, also will further the usage of 3D reconstruction from x-ray recordings, and enable wide as well as cost-effective applications. In addition, the inventive method provides the opportunity to effect a 3D reconstruction from projections that have been generated with installations of another provider.

The 3D reconstruction center that, as a matter of course, has a suitable accounting system at its disposal for use in conjunction with the creation of the 3D datasets, and that is paid by the customers for each download, can be, for example, a producer of x-ray devices that in this way offers its customers an inexpensive possibility for an expanded use of a simpler x-ray systems. Generally most doctors that employ C-arm systems wish to create such a 3D dataset in only a few instances, and as a result it is not cost-justified to install elaborate 3D software on a standard computer networked with the C-arm installation. The inventive method allows such physicians nevertheless to be able to obtain and use a 3D dataset when needed.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating a three-dimensional image dataset from a plurality of two-dimensional x-ray recordings, comprising the steps of:
    obtaining a plurality of 2D x-ray recordings of a subject, respectively at different projection directions, using an imaging facility at a first location without making a calibration from said 2D x-ray recordings of a projection geometry needed for generating a three-dimensional volume dataset from said 2D x-ray recordings, said 2D x-ray recordings being selected from the group consisting of visually observable 2D complete x-ray images from which a diagnosis of the subject can be made, and electronic data representing visually observable 2D complete x-ray images from which a diagnosis of the subject can be made;
    establishing a customer/service provider relationship between said imaging facility and a reconstruction center located remote from said first location by being physically and spatially unassociated with and separated from said first location and by being operable independently of said imaging facility, with said imaging facility as a customer and said reconstruction center as a service provider thereto;
    transmitting said plurality of 2D x-ray recordings from said first location to said reconstruction center at said second location;
    only at said reconstruction center, making said calibration from said 2D x-ray recordings of said projection geometry needed for generating said three-dimensional volume dataset from said 2D x-ray recordings and, using said calibration and said plurality of 2D x-ray recordings, generating a 3D volume dataset;
    transmitting said 3D volume dataset from said reconstruction center at said second location back to said first location; and
    substantially contemporaneously with transmitting said 3D volume dataset from said reconstruction center back to said first location, making a monetary charge to said imaging facility by said reconstruction center, based on said customer/service provider relationship, to require payment by said imaging facility to said reconstruction center at least for generating said 3D volume dataset.

2. A method as claimed in claim 1 comprising generating a video at said reconstruction center of said 3D volume dataset.

3. A method as claimed in claim 1 comprising generating specially rendered individual exposures of said 3D volume dataset at said reconstruction center.

4. A method as claimed in claim 1 comprising establishing an Internet connection between said first and second locations, and transmitting said plurality of 2D x-ray recording electronically from said first location to said second location via said Internet connection, and transmitting said 3D volume dataset from said second location to said first location via said Internet connection.

5. A method as claimed in claim 1 wherein the step of making a calibration at said reconstruction center comprises making an autocalibration at said reconstruction center using automatically detected natural landmarks in said plurality of two-dimensional x-ray recordings, and calculating respective point correspondences based on said natural landmarks.

6. A method as claimed in claim 5 comprising, at said reconstruction center, additionally calculating respective three-dimensional coordinates of said points and deriving projection parameters from the point correspondences.

7. A method as claimed in claim 1 wherein the step of making said calibration at said reconstruction center comprises manually detecting natural landmarks in said plurality of two-dimensional x-ray recordings, and making an autocalibration at said reconstruction center by calculating respective point correspondences based on the manually detected natural landmarks.

8. A method as claimed in claim 7 comprising, at said reconstruction center, additionally calculating respective three-dimensional coordinates of said points and deriving projection parameters from the point correspondences.

9. A method as claimed in claim 1 comprising the step of attaching detectable markers to said subject when generating said plurality of two-dimensional x-ray recordings, and wherein the step of making said calibration at said reconstruction center comprises making an autocalibration at said reconstruction center by automatically detecting said markers in said plurality of two-dimensional x-ray recordings and calculating respective point correspondences based on the automatically detected markers.

10. A method as claimed in claim 9 comprising, at said reconstruction center, additionally calculating respective three-dimensional coordinates of said points and deriving projection parameters from the point correspondences.

11. A method as claimed in claim 1 comprising transmitting a calibration sample with a known three-dimensional geometry from said first location to said reconstruction center at said second location together with said plurality of two-dimensional x-ray recordings, and at said reconstruction center, calculating said point correspondences from automatically detected point features and deriving projection parameters from said known three-dimensional geometry.

12. A method for generating a three-dimensional image dataset from a plurality of two-dimensional x-ray recordings, comprising the steps of:
    obtaining a plurality of 2D x-ray recordings of a subject, respectively at different projection directions, using an imaging facility at a first location without calibrating a projection geometry needed for generating a three-dimensional volume dataset from said plurality of 2D x-ray recordings, said 2D x-ray recordings being selected from the group consisting of visually observable 2D complete x-ray images from which a diagnosis of the subject can be made, and electronic data representing visually observable 2D complete x-ray images from which a diagnosis of the subject can be made;
    establishing a customer/service provider relationship between said imaging facility and a reconstruction center located remote from said first location by being physically and spatially unassociated with and separated from said first location and by being operable independently of said imaging facility, with said imaging facility as a customer and said reconstruction center as a service provider thereto;

transmitting said plurality of 2D x-ray recordings from said first location to a reconstruction center at said second location;

at said reconstruction center, automatically calibrating said projection geometry needed for generating said three-dimensional volume dataset from said plurality of 2D x-ray recordings and, using said projection geometry, calculating said 3D volume dataset from said plurality of two-dimensional x-ray recordings;

transmitting said 3D volume dataset from said reconstruction center at said second location back to said first location; and substantially contemporaneously with transmitting said 3D volume dataset from said reconstruction center back to said first location, making a monetary charge to said imaging facility by said reconstruction center, based on said customer/service provider relationship, to require payment by said imaging facility to said reconstruction center at least for generating said 3D volume dataset.

* * * * *